United States Patent
Miwa (10) Patent No.: US 6,241,680 B1
(45) Date of Patent: Jun. 5, 2001

(54) BLOOD-PRESSURE MONITORING APPARATUS

(75) Inventor: Yoshihisa Miwa, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/399,735

(22) Filed: Sep. 20, 1999

(30) Foreign Application Priority Data

Oct. 30, 1998 (JP) .................................. 10-309899

(51) Int. Cl.$^7$ ........................................ A61B 5/02
(52) U.S. Cl. ................ 600/494; 600/493; 600/490; 600/496
(58) Field of Search ..................... 600/494, 493, 600/495, 496, 490, 500, 501, 502

(56) References Cited

U.S. PATENT DOCUMENTS

| | | | | |
|---|---|---|---|---|
| 5,649,536 | * | 7/1997 | Ogura et al. | 600/590 |
| 5,759,157 | * | 6/1998 | Harada et al. | 600/494 |
| 5,772,601 | * | 6/1998 | Oka et al. | 600/495 |
| 5,776,071 | * | 7/1998 | Inukai et al. | 600/493 |
| 5,830,149 | * | 11/1998 | Oka et al. | 600/500 |
| 5,836,887 | * | 11/1998 | Ogura et al. | 600/494 |
| 5,836,888 | * | 11/1998 | Ogura et al. | 600/494 |
| 5,931,790 | * | 8/1999 | Peel, III | 600/494 |
| 6,022,320 | * | 2/2000 | Ogura et al. | 600/490 |

* cited by examiner

Primary Examiner—Eric F. Winakur
Assistant Examiner—Navin Natnithithadha
(74) Attorney, Agent, or Firm—Oliff & Berridge, PLC (57) ABSTRACT

A blood-pressure monitoring apparatus including an inflatable cuff adapted to apply a pressing pressure to a body portion of a living subject, a cuff-pulse-wave detecting device which detects a cuff pulse wave which is produced in the inflatable cuff when the cuff applies the pressing pressure to the body portion of the subject, a pressure control device which increases the pressing pressure of the inflatable cuff to a predetermined value lower than a mean blood-pressure value of the subject, an index-value calculating device for iteratively calculating an index value indicative of a condition of a circulatory system of the living subject, a starting device for judging whether each of the index values calculated by the index-value calculating device is abnormal and, when the each index value is judged as being abnormal, starting the pressure control device to increase the pressing pressure of the cuff to the predetermined value, and an abnormality judging device for judging whether the subject has an abnormal blood-pressure value, based on at least one of respective amplitudes of heartbeat-synchronous pulses of the pulse wave detected by the pulse-wave detecting device when the pressing pressure of the cuff is increased to the predetermined value by the pressure control device.

14 Claims, 6 Drawing Sheets

BLOOD-PRESSURE MONITORING APPARATUS

BACKGROUND OF THE INVENTION

1. Field of the Invention

The present invention relates to a blood-pressure monitoring apparatus which monitors the blood pressure of a living subject without causing the subject to feel serious discomfort.

2. Related Art Statement

There is known a blood-pressure ("BP") monitoring device which monitors the blood pressure of a living subject such as a patient. The BP monitoring device includes a BP measuring device which includes an inflatable cuff adapted to be wrapped around a body portion (e.g., upper arm) of a patient and which measures one or more BP values of the patient by changing the air pressure in the inflatable cuff wrapped around the upper arm of the patient. The BP monitoring device periodically starts a BP measurement of the BP measuring device at a predetermined period. However, this BP monitoring device has the problem that if the BP measuring device starts a BP measurement at a shorter period, for improving the reliability of monitoring of the BP monitoring device, the inflatable cuff more frequently presses the upper arm of the patient and causes the patient to feel serious discomfort.

In this situation, there has been proposed another BP monitoring device which includes a pulse-wave detecting device which detects a pulse wave which is produced in an inflatable cuff when the cuff presses an upper arm of a patient; a pressure control device which repeatedly increases the pressing pressure of the inflatable cuff (hereinafter, referred to as the "cuff pressure") up to a predetermined pressure value lower than a mean BP value of the patient, with a predetermined pause being inserted between each pair of repeated cuff-pressure increasing operations; a change-rate calculating means or circuit which calculates the rate of change of respective amplitudes of heartbeat-synchronous pulses of the pulse wave detected by the pulse-wave detecting device when the cuff pressure is increased to the predetermined pressure value by the pressure control device, with respect to the cuff pressure increased by the pressure control device; and an abnormality judging means or circuit which judges, based on the calculated rate of change, whether the patient has an abnormal BP value. This BP monitoring device is disclosed in, e.g., U.S. Pat. No. 5,649,536. Since the BP monitoring device changes the cuff pressure in a low pressure range from the atmospheric pressure to the predetermined pressure value, and monitors the BP of the patient based on the rate of change of the pulse amplitudes obtained during the changing of the cuff pressure, it does not cause the patient to feel serious discomfort.

However, even in the above-indicated second BP monitoring device, the inflatable cuff repeatedly presses the upper arm of the patient, though the pressing pressure of the cuff, i.e., the cuff pressure is not increased to a high pressure value. If the frequency of pressing of the cuff is increased to improve the reliability of the BP monitoring device, the patient may feel serious discomfort.

Meanwhile, there has also been proposed yet another BP monitoring device which iteratively calculates an index value indicative of a condition of a circulatory system of a patient and monitors a change of the BP of the patient based on a change of each of the calculated index values. The index value may be one which is indicative of a condition of circulation of blood in the patient and which can be non-invasively obtained without pressing any body portions of the patient. For example, the index value may be a piece of pulse-wave-propagation ("PWP") relating information, such as a PWP velocity or a PWP time, that relates to propagation of a pulse wave through an arterial vessel of the patient; a piece of pulse-relating information, such as a pulse rate (i.e., heart rate) or a pulse period; or a piece of blood-flow-amount-relating information, such as a peripheral-pulse-wave area, that relates to an amount of flow of blood through a peripheral body portion of the patient. The third BP monitoring device is disclosed in, e.g., U.S. Pat. No. 5,776,071. The disclosed BP monitoring device iteratively calculates, as the index value, a value relating to each of heartbeat-synchronous pulses of a volumetric pulse wave obtained from a patient, and monitors the BP of the patient based on a change of each calculated value. When the third BP monitoring device finds a significant change of each calculated value (i.e., each index value), it starts a BP measurement of a BP measuring device using an inflatable cuff, so as to obtain one or more reliable BP values of the patient. However, if too low a reference value is employed to find a change of each index value, for the purpose of improving the reliability of the BP monitoring device, the cuff would too frequently press the upper arm of the patient and would cause the patient to feel serious discomfort.

SUMMARY OF THE INVENTION

It is therefore an object of the present invention to provide a blood-pressure monitoring apparatus which monitors the blood pressure of a living subject with a high reliability without causing the subject to feel serious discomfort.

The present invention provides a blood-pressure monitoring apparatus which has one or more of the technical features that are described below in respective paragraphs given parenthesized sequential numbers (1) to (14). Any technical feature which includes another technical feature shall do so by referring, at the beginning, to the parenthesized sequential number given to that technical feature.

(1) According to a first feature of the present invention, there is provided a blood-pressure monitoring apparatus comprising an inflatable cuff adapted to apply a pressing pressure to a body portion of a living subject; a cuff-pulse-wave detecting device which detects a cuff pulse wave which is produced in the inflatable cuff when the inflatable cuff applies the pressing pressure to the body portion of the living subject, the cuff pulse wave comprising a plurality of heartbeat-synchronous pulses; a pressure control device which increases the pressing pressure of the inflatable cuff to a predetermined value lower than a mean blood-pressure value of the living subject; index-value calculating means for iteratively calculating an index value indicative of a condition of a circulatory system of the living subject; starting means for judging whether each of the index values calculated by the index-value calculating means is abnormal and, when the each index value is judged as being abnormal, starting the pressure control device to increase the pressing pressure of the inflatable cuff to the predetermined value; change-rate calculating means for calculating a rate of change of respective amplitudes of the heartbeat-synchronous pulses of the pulse wave detected by the pulse-wave detecting device when the pressing pressure of the inflatable cuff is increased to the predetermined value by the pressure control device, with respect to the pressing pressure of the inflatable cuff increased by the pressure control device; and abnormality judging means for judging, based on the calculated rate of change, whether the living subject has an abnormal blood-pressure value. In the present BP monitoring apparatus, the pressure control device increases the pressing pressure of the inflatable cuff, for judging whether the BP of the subject is abnormal, when the calculated index value indicative of the condition of the circulatory system of the subject is judged as being abnormal, i.e., there is a great possibility that the BP of the subject is abnormal. Thus, in the present apparatus, the cuff less frequently presses the body portion of the subject than a conventional apparatus in which a cuff periodically presses a body portion of a subject at a predetermined short period. In addition, the present apparatus can monitor the BP of the subject with a high reliability.

(2) According to a second feature of the present invention that includes the first feature (1), the monitoring apparatus further comprises a measuring device which measures a blood-pressure value of the living subject by changing the pressing pressure of the inflatable cuff, the abnormality judging means comprises starting means for starting, when the living subject is judged as having the abnormal blood-pressure value, a blood-pressure measurement of the measuring device. In the present BP monitoring apparatus, when the abnormality judging means judges that the subject has an abnormal BP value, an accurate BP value of the subject is immediately measured by the measuring device using the cuff. Based on this accurate BP value of the subject, a person who attends to the subject can give appropriate treatments to the subject. In addition, even if the calculated index value may be judged as being abnormal, the present apparatus does not immediately start a BP measurement of the measuring device, in contrast to a conventional apparatus in which a cuff is immediately inflated for measuring a BP value of a subject. In fact, in that case, the present apparatus increases the cuff pressure in a predetermined low pressure range, for judging whether the BP of the subject is abnormal. Accordingly, even though a low reference value or a narrow reference range may be employed to find an abnormal index value, the cuff does not so frequently press the body portion of the subject and therefore does not cause the subject to feel serious discomfort.

(3) According to a third feature of the present invention that includes the first or second feature (1) or (2), the monitoring apparatus further comprises a periodically measuring device which periodically measures, at a predetermined period, a blood-pressure value of the living subject by changing the pressing pressure of the inflatable cuff. In this case, the predetermined period may be much longer than that employed in a conventional apparatus.

(4) According to a fourth feature of the present invention that includes any one of the first to third features (1) to (3), the index-value calculating means comprises a volumetric-pulse-wave sensor which detects a volumetric pulse wave from a peripheral body portion of the living subject, the volumetric pulse wave comprising a plurality of heartbeat-synchronous pulses; and pulse-wave-area-relating-value calculating means for iteratively calculating, as the each index value, a value relating to an area of each of the heartbeat-synchronous pulses of the volumetric pulse wave. The value relating to the area may be the area itself, or a value obtained by normalizing the area.

(5) According to a fifth feature of the present invention that includes any one of the first to fourth features (1) to (4), the starting means comprises change-value calculating means for iteratively calculating a change value relating to a change of the each index value from a value based on at least one prior index value; judging means for judging, when the calculated change value does not fall within a reference range, that the each index value is abnormal; and control means for starting the pressure control device to increase the pressing pressure of the inflatable cuff to the predetermined value. The change value relating to the change of each index value may be an amount of change of the each index value from a "control" index value which is calculated prior to the each index value by the index-value calculating means, or from a moving average of a predetermined number of successive index values which are lately calculated by the index-value calculating means and which may, or may not, include the each index value. Alternatively, the change value may be the ratio (e.g., percentage) of the amount of change of the each index value to the "control" index value or the moving average. The reference range may be replaced with a single reference value. In the latter case, the judging means judges, when the calculated change value is greater (or smaller) than the reference value, that the each index value is abnormal.

(6) According to a sixth feature of the present invention that includes any one of the first to fifth features (1) to (5), the change-rate calculating means comprises a memory which stores the respective amplitudes of the heartbeat-synchronous pulses of the pulse wave detected by the pulse-wave detecting device when the pressing pressure of the inflatable cuff is increased to the predetermined value by the pressure control device.

(7) According to a seventh feature of the present invention that includes any one of the first to sixth features (1) to (6), the abnormality judging means comprises judging means for judging, when the calculated rate of change is greater than a predetermined value, that the living subject has the abnormal blood-pressure value.

(8) According to an eighth feature of the present invention that includes any one of the first to seventh features (1) to (7), the abnormality judging means comprises judging means for judging that the living subject has the abnormal blood-pressure value, when a greatest one of the respective amplitudes of the heartbeat-synchronous pulses of the pulse wave detected by the pulse-wave detecting device when the pressing pressure of the inflatable cuff is increased to the predetermined value by the pressure control device is smaller than a predetermined value. In this case, the judging means may judge that the subject has fallen in medical or clinical shock.

(9) According to a ninth feature of the present invention that includes any one of the first to eighth features (1) to (8), the monitoring apparatus further comprises an informing device which informs, when the abnormality judging means judges that the living subject has the abnormal blood-pressure value, a person of an occurrence of abnormality to the blood pressure of the living subject. In this case, the person can give appropriate treatments to the subject.

(10) According to a tenth feature of the present invention that includes any one of the first to ninth features (1) to (9), the starting means comprises judging means for judging that the each index value is abnormal, when a value based on the each index value satisfies a predetermined condition with respect to at least one predetermined value. The value based on the each index value may be the each index value itself, or a change value of the each index value from a value based on at least one prior value. The predetermined condition may be a first condition that the value based on the each index value does not fall within a reference range whose upper and lower limit values S are equal to two predetermined values, respectively; a second condition that the value based on the each index value is greater than the predetermined value; or a third condition that the value based on the each index value is smaller than the predetermined value.

(11) According to an eleventh feature of the present invention that includes any one of the first to tenth features (1) to (10), the abnormality judging means comprises judging means for judging that the living subject has the abnormal blood-pressure value, when the calculated rate of change satisfies a predetermined condition with respect to at least one predetermined value. The predetermined condition may be a first condition that the calculated rate of change does not fall within a reference range whose upper and lower limit values are equal to two predetermined values, respectively; a second condition that the calculated rate of change is greater than the predetermined value; or a third condition that the calculated rate of change is smaller than the predetermined value.

(12). According to a twelfth feature of the present invention, there is provided a blood-pressure monitoring apparatus comprising an inflatable cuff adapted to apply a pressing pressure to a body portion of a living subject; a cuff-pulse-wave detecting device which detects a cuff pulse wave which is produced in the inflatable cuff when the cuff applies the pressing pressure to the body portion of the living subject, the cuff pulse wave comprising a plurality of heartbeat-synchronous pulses; a pressure control device which increases the pressing pressure of the inflatable cuff to a predetermined value lower than a mean blood-pressure value of the living subject; index-value calculating means for iteratively calculating an index value indicative of a condition of a circulatory system of the living subject; starting means for judging whether each of the index values calculated by the index-value calculating means is abnormal and, when the each index value is judged as being abnormal, starting the pressure control device to increase the pressing pressure of the inflatable cuff to the predetermined value; and abnormality judging means for judging whether the living subject has an abnormal blood-pressure value, based on at least one of respective amplitudes of the heartbeat-synchronous pulses of the pulse wave detected by the pulse-wave detecting device when the pressing pressure of the inflatable cuff is increased to the predetermined value by the pressure control device. The present BP monitoring apparatus enjoys the same advantages as those of the BP monitoring apparatus in accordance with the first feature (1).

(13) According to a thirteenth feature of the present invention that includes the twelfth feature (12), the monitoring apparatus further comprises change-rate calculating means for calculating a rate of change of the respective amplitudes of the heartbeat-synchronous pulses of the pulse wave detected by the pulse-wave detecting device when the pressing pressure of the inflatable cuff is increased to the predetermined value by the pressure control device, with respect to the pressing pressure of the inflatable cuff increased by the pressure control device, and the abnormality judging means comprises judging means for judging, based on the calculated rate of change, whether the living subject has the abnormal blood-pressure value.

(14) According to a fourteenth feature of the present invention that includes the twelfth or thirteenth feature (12) or (13), the abnormality judging means comprises judging means for judging whether the living subject has the abnormal blood-pressure value, based on a greatest one of the respective amplitudes of the heartbeat-synchronous pulses of the pulse wave detected by the pulse-wave detecting device when the pressing pressure of the inflatable cuff is increased to the predetermined value by the pressure control device.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
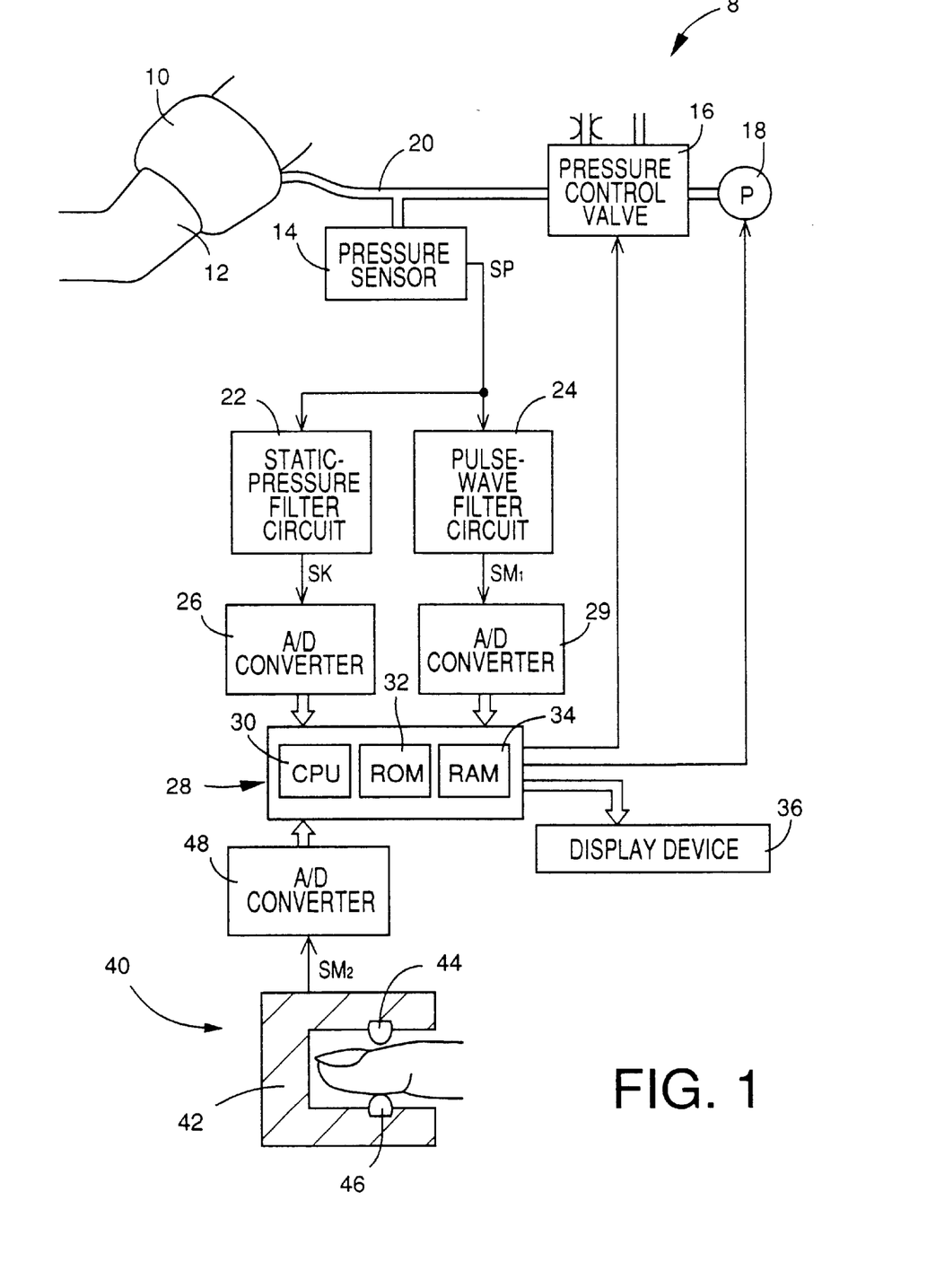
FIG. 1 is a diagrammatic view of a blood-pressure ("BP") monitoring apparatus embodying the present invention.

Referring to FIG. 1, there will be described a blood-pressure ("BP") monitoring apparatus 8 embodying the present invention.

In FIG. 1, the BP monitoring apparatus 8 includes an inflatable cuff 10 which has a belt-like cloth bag and a rubber bag accommodated in the cloth bag and which is adapted to be wrapped around, e.g., a right upper arm 12 of a patient as a living subject, and a pressure sensor 14, a pressure control valve 16 and an air pump 18 each of which is connected to the cuff 10 via piping 20. The pressure control valve 16 is selectively placed in an inflation position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure in the inflatable cuff 10, and supplies a pressure signal SP representative of the detected pressure to each of a static-pressure filter circuit 22 and a pulse-wave filter circuit 24. The static-pressure filter circuit 22 includes a low-pass filter and extracts, from the pressure signal SP, a static component $P_C$ contained in the signal SP, i.e., cuff-pressure signal SK representative of the static cuff pressure. The cuff-pressure signal SK is supplied to an electronic control device 28 via an analog-to-digital ("A/D") converter 26.

Figure 2:
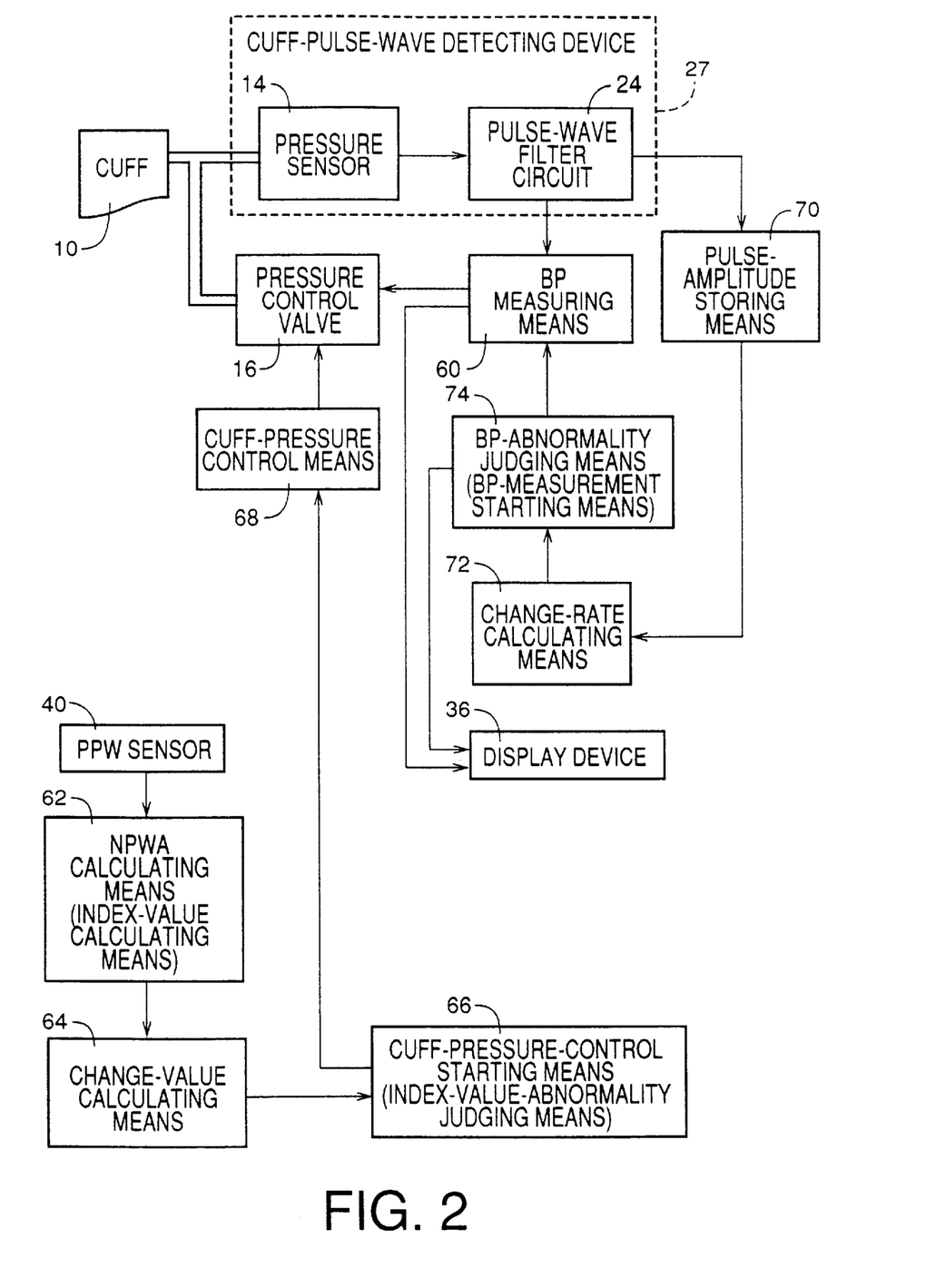
FIG. 2 is a block diagram for illustrating essential functions of an electronic control device of the apparatus of FIG. 1.

The pulse-wave filter circuit 24 includes a band-pass filter and extracts, from the pressure signal SP, an oscillatory component having predetermined frequencies, i.e., cuff-pulse-wave signal $SM_1$. The cuff-pulse-wave signal $SM_1$ is supplied to the control device 28 via an A/D converter 29. The cuff-pulse-wave signal $SM_1$ is representative of the cuff pulse wave, i.e., oscillatory pressure wave which is produced from a brachial artery (not shown) of the patient in synchronism with the heartbeat of the patient and is propagated to the inflatable cuff 10. Thus, the pressure sensor 14 and the pulse-wave filter circuit 24 cooperate with each other to provide a cuff-pulse-wave detecting device 27 (FIG. 2).

The control device 28 is provided by a so-called microcomputer including a central processing unit ("CPU") 30, a read only memory ("ROM") 32, a random access memory ("RAM") 34, and an input-and-output ("I/O") port (not shown). The CPU 30 processes signals according to control programs pre-stored in the ROM 32 by utilizing a temporary-storage function of the RAM 34, and supplies drive signals to the pressure control valve 16 and the air pump 18 through the I/O port. In addition, the CPU 30 controls the contents of a screen image displayed by a display device 36 (e.g., cathode ray tube).

The BP monitoring apparatus 8 further includes a photoelectric-pulse-wave ("PPW") sensor 40 as a volumetric-pulse-wave detecting device which monitors the condition of circulation of blood through a peripheral body portion of the patient, by detecting a volumetric pulse wave (i.e., plethysmogram) from a peripheral blood vessel or vessels of the patient. The PPW sensor 40 may be one which is employed in a known plethysmograph device.

The PPW sensor 40 includes a housing 42 which accommodates a peripheral body portion of the patient, e.g., an end portion of a finger of a left hand of the patient. The PPW sensor 40 is preferably worn on the hand of one arm different from the other arm around which the cuff 10 is wrapped. The PPW sensor 40 additionally includes a light emitting element 44, such as LED (light emitting diode), which is disposed on an inner wall of the housing 42; and a light receiving element 46, such as a photodiode or a phototransister, which is disposed on the opposite inner wall of the housing 42. The light emitting element 44 as a light source emits, toward the body surface or skin of the patient, a red or infrared light in a wavelength range that can be reflected by hemoglobin, preferably, an infrared light having the wavelength of about 800 nm whose absorbance does not change depending on the degree of blood oxygen saturation of the patient. The light emitted toward the body surface by the light emitting element 44 transmits through the tissue of the peripheral body portion (i.e., finger) of the patient where a dense capillaries occur, and the light which has transmitted through the tissue is received or detected by the light receiving element 46.

The light receiving element 46 outputs a photoelectric-pulse-wave ("PPW") signal $SM_2$ which is representative of a photoelectric pulse wave ("PPW") corresponding to the amount of light received from the tissue of the patient, i.e., the amount or volume of blood flowing through the capillaries of the tissue. The light receiving element 46 outputs the PPW signal $SM_2$ to the control device 28 via an A/D converter 48.

FIG. 2 illustrates essential functions of the control device 28 of the present BP monitoring apparatus 8.

In the figure, a BP measuring means or circuit 60 measures, by controlling the air pump 18 and the pressure control valve 16, a systolic, a mean, and a diastolic BP value $BP_{SYS}$, $BP_{MEAN}$, $BP_{DIA}$ of the patient, according to a well known oscillometric method, based on the variation of respective amplitudes of heartbeat-synchronous pulses of the cuff pulse wave represented by the cuff-pulse-wave signal $SM_1$ obtained from the cuff 10 wrapped around the upper arm of the patient while the cuff pressure which is quickly increased to a target pressure value $P_{CM}$ (e.g., 180 mmHg), is slowly decreased at a predetermined rate, e.g., the rate of about 3 mmHg/sec. The BP measuring means 60 controls the display device 36 to display the thus measured BP values $BP_{SYS}$, $BP_{MEAN}$, $BP_{DIA}$.

Figure 3:
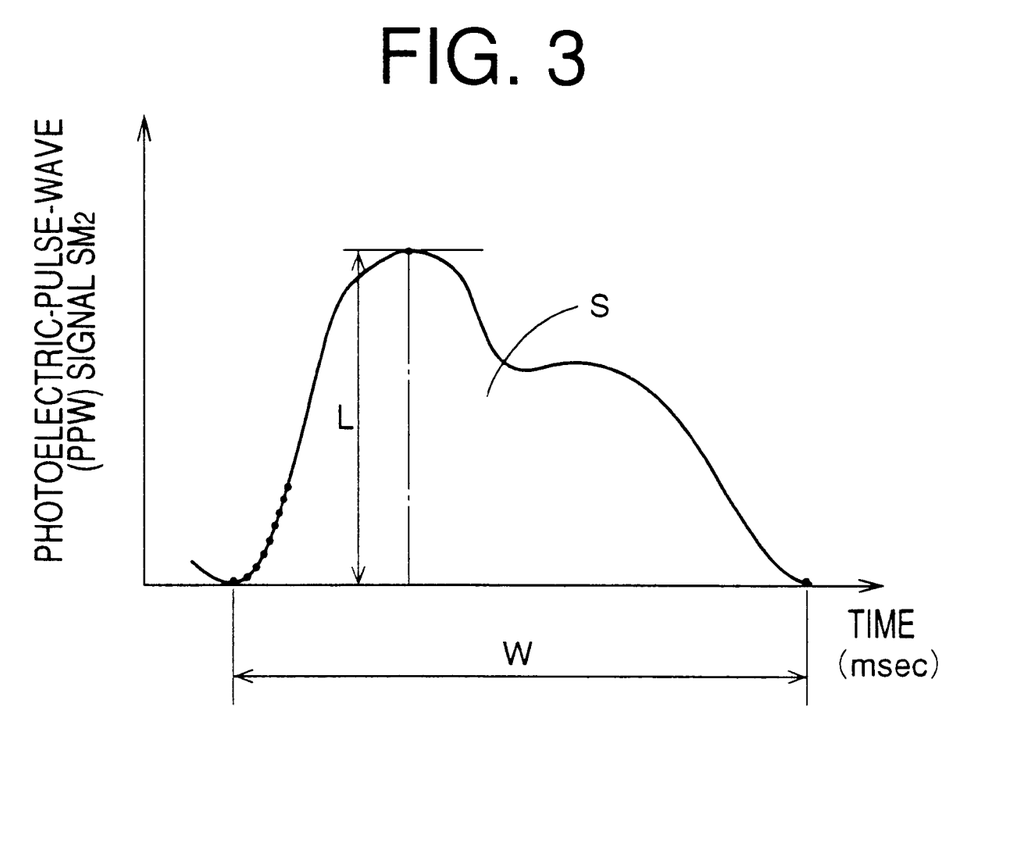
FIG. 3 is a view for illustrating a photoelectric pulse wave which is detected by a photoelectric-pulse-wave sensor of the apparatus of FIG. 1.

A normalized-pulse-wave-area ("NPWA") calculating means or circuit 62 functions as part of a circulatory-system-condition-index-value calculating means which successively calculates an index value indicative of a condition of the circulatory system of the patient. More specifically described, the NPWA calculating means 62 successively calculates, as the index value, a normalized pulse-wave area ("NPWA") value $S_F$ by normalizing an area S defined or enveloped by the waveform of each of successive heartbeat-synchronous pulses of the PPW (i.e., PPW signal $SM_2$) detected by the PPW sensor 40, based on a period W and an amplitude L of the each pulse. As shown in FIG. 3, the waveform of each pulse of the PPW (i.e., PPW signal $SM_2$) is defined by a series of data points indicative of respective magnitudes which are input at a predetermined short interval such as several milliseconds to several tens of milliseconds. The pulse-wave area S is obtained by integrating, over the period W of the each pulse, respective magnitudes of the data points of the each pulse, and then a NPWA value $S_F$ is obtained according to the following expression: $S_F = S/(W \times L)$. The NPWA value $S_F$ is a dimensionless value indicative of the ratio of the pulse-wave area S to a rectangular area defined by the period W and the amplitude L of the each pulse. For this parameter, the symbol "% MAP" may be used in place of the symbol "$S_F$".

A change-value calculating means or circuit 64 calculates a change value $\Delta D$ that is an amount of change of each NPWA value $S_F$ successively calculated by the NPWA calculating means 62, from the "control" NPWA value $S_F$ calculated at the time of the last BP measuring operation, or the ratio of the amount of change to the control NPWA value $S_F$. The "control" NPWA value $S_F$ may be replaced with a moving average $S_{FAV}$ of a predetermined number of successive NPWA values $S_F$ including the each NPWA value $S_F$.

A cuff-pressure-control starting means 66 functions as index-value-abnormality judging means which judges, when the absolute value of the change value $\Delta D$ calculated by the change-value calculating means 64 is greater than a predetermined reference value $D_0$, that each NPWA value $S_F$ successively calculated by the NPWA calculating means 62 is abnormal, and starts a cuff-pressure control of a cuff-pressure control means or circuit 68 described below.

The cuff-pressure control means 68 controls, when the cuff-pressure-control starting means 66 judges that each NPWA value $S_F$ is abnormal, the air pump 18 and the pressure control valve 16 so as to increase the pressing pressure of the cuff 10 up to a predetermined low pressure value $P_1$ sufficiently lower than a mean BP value $BP_{MEAN}$ of the patient and subsequently quickly decrease the cuff pressure $P_C$ down to the atmospheric pressure.

A pulse-amplitude storing means or circuit 70 stores, in a region (not shown) of the RAM 34, respective amplitudes $A_m$ of heartbeat-synchronous pulses of the cuff pulse wave (i.e., cuff-pulse-wave signal $SM_1$) detected by the pulse-wave filter circuit 24 while the cuff pressure $P_C$ is increased up to the low pressure value $P_1$ by the cuff-pressure control means 68.

Figure 4:
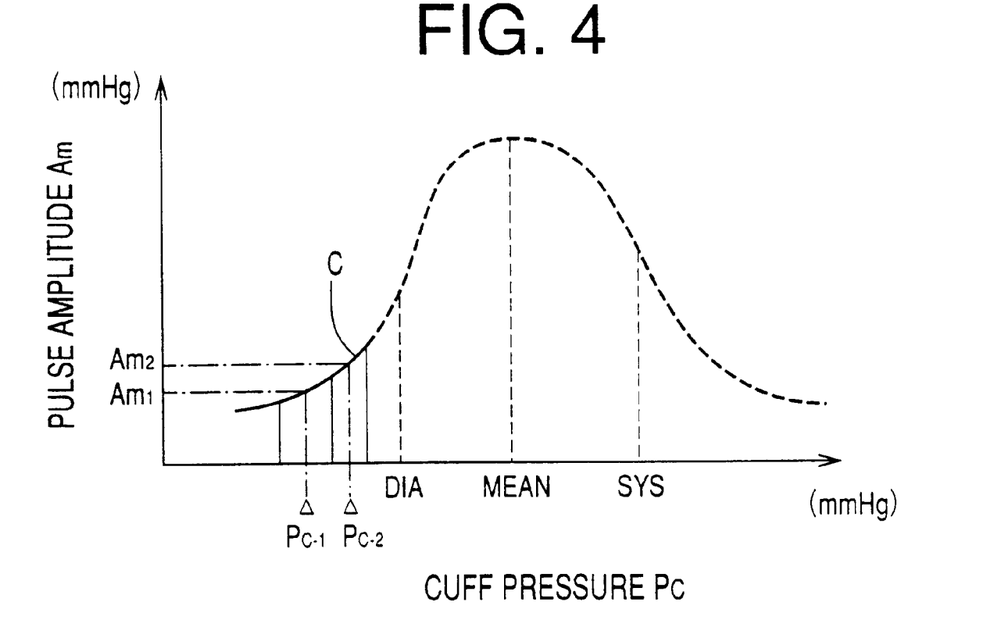
FIG. 4 is a view for illustrating a manner in which a change-rate calculating means of the apparatus of FIG. 1 calculates the rate of change of respective amplitudes of heartbeat-synchronous pulses of a pulse wave detected from an inflatable cuff of the apparatus of FIG. 1.

A change-value calculating means or circuit 72 calculates the rate of change $\Theta$ of the respective pulse amplitudes $A_m$ of the cuff pulse wave stored in the RAM 34, with respect to the cuff pressure PC increased by the cuff-pressure control means 68. For example, the rate of change $\Theta$ may be calculated as the angle of inclination of a straight line tangential to the envelope C of the respective pulse amplitudes $A_m$ of the cuff pulse wave (stored in the RAM 34) with respect to the cuff pressure $P_C$. Regarding an envelope C shown in FIG. 4, the rate of change $\Theta$, i.e., the angle of inclination $\Theta$ is calculated based on two pulse amplitudes $A_{m1}$, $A_{m2}$ respectively corresponding to two predetermined cuff pressure values $P_{C-1}$, $P_{C-2}$, according to the following expression (1):

$$\Theta=(A_{m2}-A_{m1})/(P_{C-2}-P_{C-1}) \quad \ldots (1)$$

The two cuff pressure values $P_{C-1}$, $P_{C-2}$ are predetermined or pre-selected such that the values $P_{C-1}$, $P_{C-2}$ correspond to a rising portion of the envelope C (i.e., pulse amplitudes $A_m$) that largely changes as the cuff pressure $P_C$ changes under a diastolic BP value $BP_{DIA}$ of the patient.

Alternatively, the change-value calculating means 72 may calculate the rate of change $\Theta$ or the angle of inclination $\Theta$, by first selecting, from all the pulse amplitudes $A_m$ stored in the RAM 34, two or more pulse amplitudes $A_m$ in such a manner that the above-indicated two predetermined cuff pressure values $P_{C-1}$, $P_{C-2}$ fall within a cuff pressure range which is defined by the greatest and smallest ones of respective cuff pressure values corresponding to those selected pulse amplitudes $A_m$ and which is as narrow as possible, and second determining, as the change rate $\Theta$, the angle of inclination of a straight line L approximating those selected pulse amplitudes $A_m$.

A BP-abnormality judging means or circuit 74 judges, based on the rate of change $\Theta$ calculated by the change-rate calculating means 72, whether the patient has an abnormal BP value. When the patient is judged as having an abnormal BP value, the BP-abnormality judging means 74 starts a BP measurement of the BP measuring means 60. Thus, the BP-abnormality judging means 74 also functions as a BP-measurement starting means.

Figure 5:
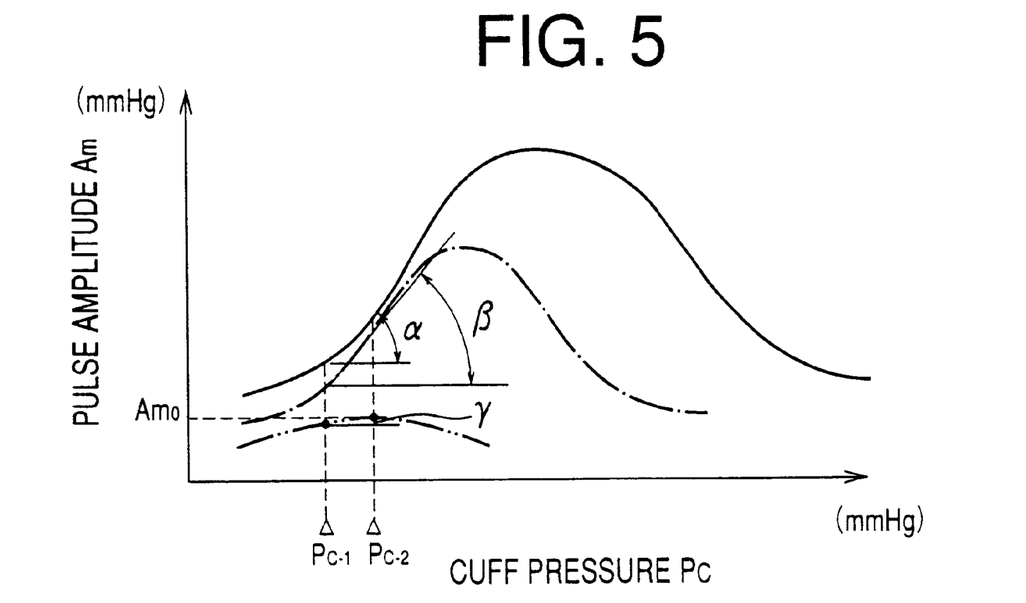
FIG. 5 is a view for explaining the fact that the envelope of respective amplitudes of heartbeat-synchronous pulses of a pulse wave changes as the BP of a living subject changes.

FIG. 5 shows that it is possible to judge or find an abnormality of the BP of the patient based on the rate of change $\Theta$ of the pulse amplitudes $A_m$ of the cuff pulse wave. FIG. 5 shows three envelopes of pulse amplitudes $A_m$ that are obtained from three persons having different BP values, respectively. The envelope of pulse amplitudes $A_m$ that is obtained from the person having a normal BP value is indicated at solid line. The rising portion of this envelope has an angle a of inclination of a straight line passing through two pulse amplitudes $A_m$ respectively corresponding to the two predetermined cuff pressure values $P_{C-1}$, $P_{C-2}$. In contrast, the envelope of pulse amplitudes $A_m$ that is obtained from the person having an excessively low BP value, indicated at one-dot chain line, is smaller than that obtained from the normal person, and is biased toward the left, i.e., low BP values. Thus, a straight line determined for the rising portion of the second envelope has an angle β greater than the angle α. Based on this fact, the BP-abnormality judging means 74 judges that the BP of the patient is abnormally low, when the rate of change $\Theta$ is greater than a first predetermined reference value $\Theta_0$. On the other hand, a straight line determined for the rising portion of the third envelope of pulse amplitudes $A_m$ that is obtained from the person who has fallen in shock, indicated at two-dot chain line, has an angle γ smaller than the angle α. Since, however, the pulse amplitudes $A_m$ defining the third envelope are much smaller than those defining the first envelope. Based on this fact, the BP-abnormality judging means 74 judges that the BP of the patient is abnormally low, when the maximum pulse amplitude $A_{mMAX}$ is smaller than a predetermined reference value $A_{m0}$. In either case, when the BP of the patient is judged as being abnormal, the BP-abnormality judging means 74 starts a BP measurement of the BP measuring means 60 so that an accurate BP value of the patient may be measured using the inflatable cuff 10.

Figure 6:
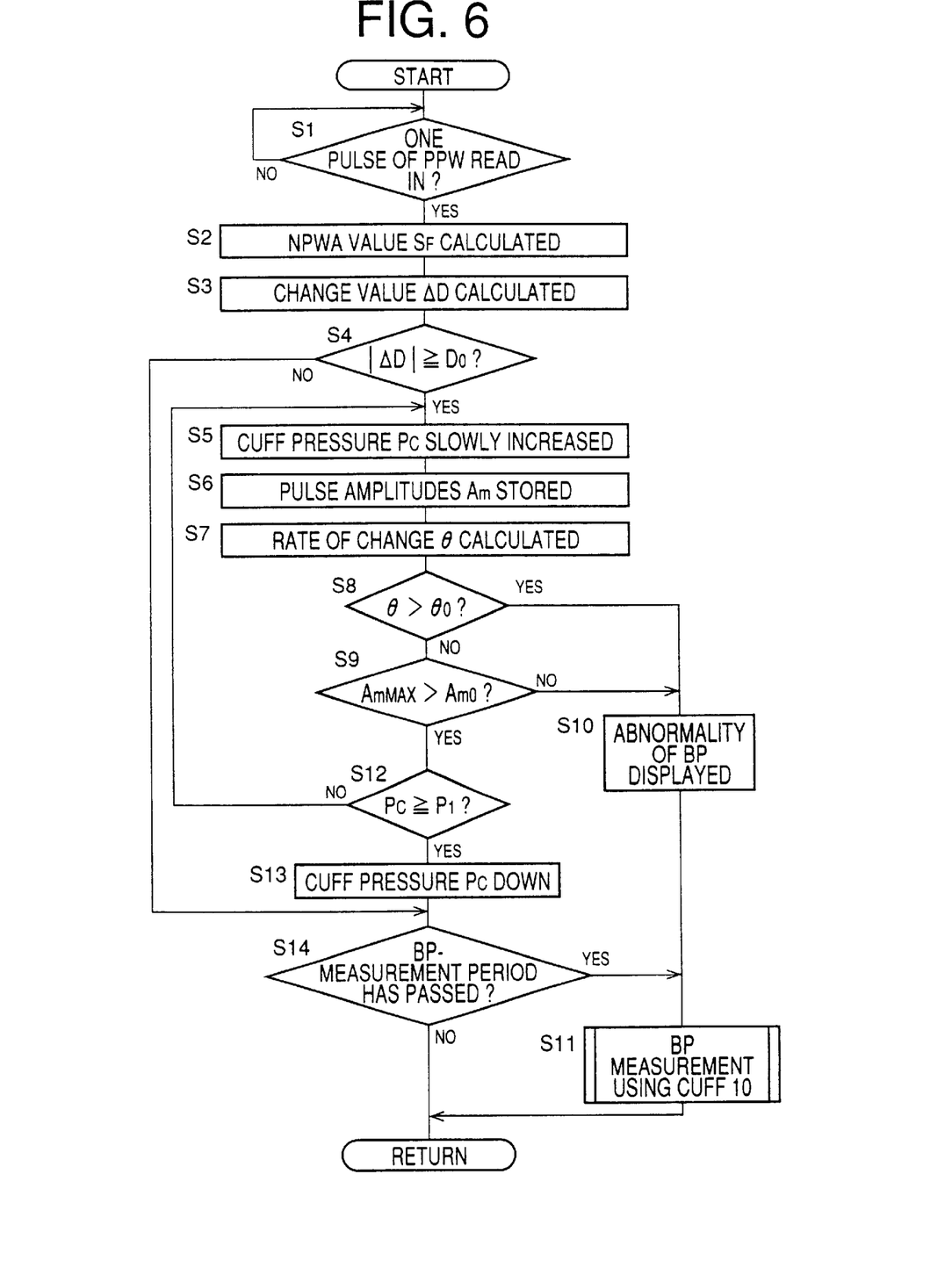
FIG. 6 is a flow chart representing a control program according to which the control device of the apparatus of FIG. 1 is operated for monitoring the BP of the living subject.

FIG. 6 is a flow chart representing a control program according to which the control device 28 of the BP monitoring apparatus 8 is operated.

First, at Step S1, the CPU 30 of the control device 28 judges whether the waveform of one heartbeat-synchronous pulse of the photoelectric pulse wave ("PPW") has been read in as the PPW signal $SM_2$ through the PPW sensor 40. If a negative judgment is made at Step S1, the CPU 30 waits till a positive judgment is made. Meanwhile, if a positive judgment is made at Step S1, the control of the CPU 30 goes to Step S2 corresponding to normalized-pulse-wave-area ("NPWA") calculating means 62. At Step S2, the CPU 30 calculates an area S, a period W, and an amplitude L of the waveform of the one pulse of the PPW read in at Step S1, and calculates an NPWA value $S_F$ according to the following expression: $S_F=S/(W\times L)$.

Step S2 is followed by Step S3 corresponding to the change-value calculating means 64. At Step S3, the CPU 30 calculates a change value $\Delta D$, e.g., an amount of change of the NPWA value $S_F$ calculated at Step S2, from the "control" NPWA value $S_{Fm}$ calculated at the time of the last BP measuring operation using the cuff 10, according to the following expression: $\Delta D=S_F-S_{Fm}$. Alternatively, the CPU 30 may calculate, as the change value $\Delta D$, an amount of change of the NPWA value $S_{Fi}$ calculated at Step S2 in the current control cycle according to the flow chart of FIG. 6, from a moving average $S_{FAV}$ of a predetermined number (i.e., n+1) of NPWA values calculated at Step S2 in the same number of control cycles, according to the following expression: $\Delta D=S_{Fi}-S_{FAV}=S_{Fi}-(S_{Fi-n}+ \ldots +S_{Fi-1}+S_{Fi})/(n+1)$. Otherwise, the CPU 30 may calculate, as the change value $\Delta D$, a ratio of an amount of change of the NPWA value $S_F$ calculated at Step S2, from the "control" NPWA value $S_{Fm}$, to the "control" NPWA value $S_{Fm}$, according to the following expression: $\Delta D=(S_F-S_{Fm})/S_{Fm}$.

Step S3 is followed by Step S4 corresponding to the cuff-pressure-control starting means 66. At Step S4, the CPU 30 judges whether the absolute value of the change value $\Delta D$ calculated at Step S3 is not smaller than a predetermined reference value $D_0$. This reference value $D_0$ is empirically or experimentally obtained in advance as a criterion value which can be used in judging whether the NPWA value $S_F$ corresponding to the BP of the patient has so largely changed that an accurate BP value of the patient should be measured using the cuff 10. In the case where the change value $\Delta D$ is calculated as the ratio (i.e., percentage) of the amount of change of the NPWA value $S_F$ calculated at Step S2, from the "control" NPWA value $S_{Fm}$, to the "control" NPWA value $S_{Fm}$, according to the expression: $\Delta D=(S_F-S_{Fm})/S_{Fm}$, the reference value $D_0$ is predetermined at from 20 % to 30%, preferably, at 25 %.

If a negative judgment is made at Step S4, the control of the CPU 30 goes to Step S14 described later. On the other hand, if a positive judgment is made at Step S4, there is a great possibility that the BP of the patient is abnormal.

Hence, the control of the CPU 30 goes to Step S5 corresponding to the cuff-pressure control means 68, so as to judge whether the BP of the patient is abnormal by increasing the cuff pressure $P_C$ up to only a predetermined low pressure value $P_1$ sufficiently lower than a mean BP value $BP_{MEAN}$ of the patient. At Step S5, the CPU 30 operates the air pump 18 and the pressure control valve 16 to slowly increase the cuff pressure $P_C$ at a predetermined rate, e.g., 3 mmHg/sec. This pressure-increase rate is selected such that at least two heartbeat-synchronous pulses, preferably not less than three pulses, of the cuff pulse wave can be produced in the cuff 10 and detected by the pressure sensor 14 while the cuff pressure $P_C$ is increased at the selected rate up to the predetermined low pressure value $P_1$.

Figure 7:
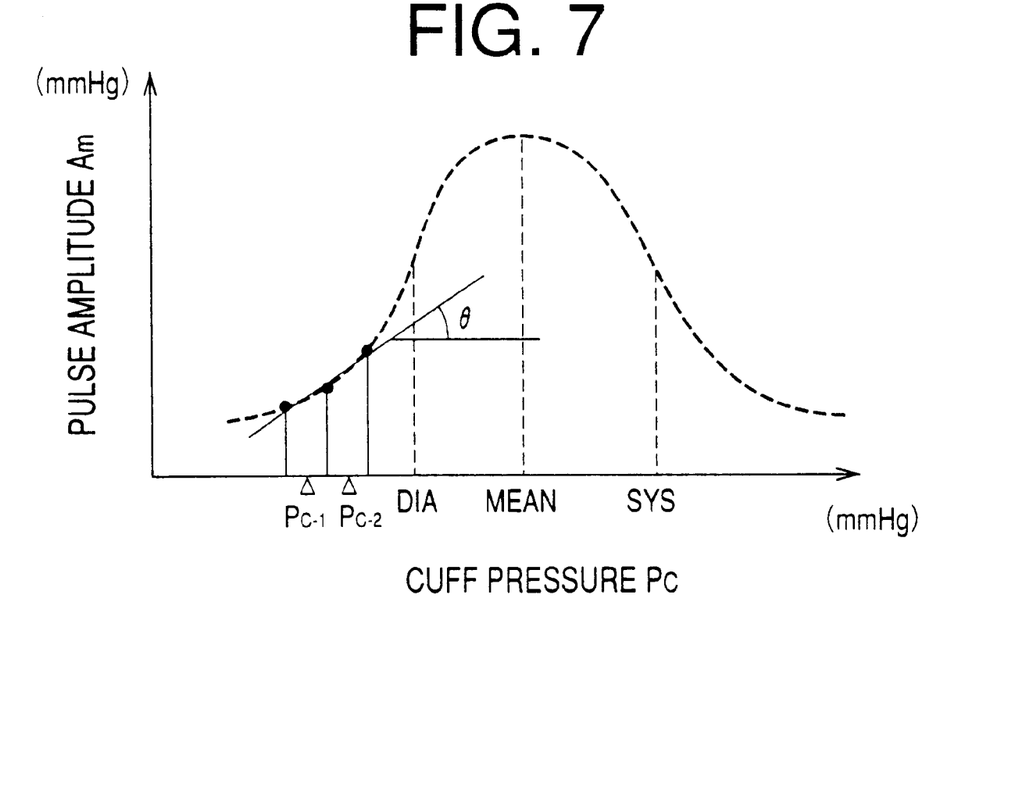
FIG. 7 is a view for illustrating a manner in which the rate of change of the respective amplitudes of heartbeat-synchronous pulses of the pulse wave detected from the cuff is calculated at Step S7 of the flow chart of FIG. 6.

Step S6 is followed by Step S7 corresponding to the pulse-amplitude storing means 70. At Step S7, the CPU 30 stores, in a certain region of the RAM 34, the amplitude $A_m$ of each heartbeat-synchronous pulse produced in the cuff 10. Step S6 is followed by Step S7 corresponding to the change-value calculating means 72. At Step S7, the CPU 30 determines a straight line approximating a rising portion of the envelope of respective amplitudes $A_m$ of the heartbeat-synchronous pulses produced in the cuff 10. More specifically described, as shown in FIG. 7, the CPU 30 selects, from all the pulse amplitudes $A_m$ stored in the RAM 34 at Step S6, a first pulse amplitude $A_m$ obtained immediately before the cuff pressure $P_C$ reaches the first predetermined pressure value $P_{C-1}$ a second pulse amplitude Am obtained after the cuff pressure $P_C$ reaches the first predetermined pressure value $P_{C-1}$ and before the cuff pressure $P_C$ reaches the second predetermined pressure value $P_{C-2}$, and a third pulse amplitude $A_m$ obtained immediately after the cuff pressure $P_C$ reaches the second predetermined pressure value $P_{C-2}$, and determines a straight line approximating the three pulse amplitude $A_m$ according to the method of least squares. Finally, the CPU 30 determines the angle of inclination (i.e., slope) of the straight line, as the rate of change $\Theta$ of the pulse amplitudes $A_m$ with respect to the cuff pressure $P_C$.

Step S7 is followed by Steps S8 and S9 corresponding to the BP-abnormality judging means 74. First, at Step S8, the CPU 30 judges whether the rate of change $\Theta$ calculated at Step S7 is greater than a predetermined reference value $\Theta_0$. This reference value $\Theta_0$ may be equal to the angle $\beta$ of the rising portion of the envelope, indicated at one-dot chain line in FIG. 5, obtained from the person having excessively low BP values, e.g., systolic BP value of 90 mmHg and diastolic BP value of 50 mmHg. The angle $\beta$ is determined as the angle of inclination (i.e., slope) $\Theta$ of a straight line passing through two pulse amplitudes $A_m$ respectively corresponding to the two predetermined cuff pressure values $P_{C-1}$, $P_{C-2}$, according to the first expression (1).

If a negative judgment is made at Step S8, the control of the CPU 30 goes to Step S9 to judge whether the greatest or maximum pulse amplitude $A_{mMAX}$ of all the pulse amplitudes $A_m$ stored in the RAM 34 at Step S6 is greater than a predetermined reference value $A_{m0}$. This reference value $A_{m0}$ may be equal to the pulse amplitude $A_m$ corresponding to the predetermined cuff pressure value $P_{C-2}$, on the envelope, indicated at two-dot chain line in FIG. 5, obtained from the person who has fallen in shock.

If a positive judgment is made at Step S8, or if a negative judgment is made at Step S9, the control of the CPU 30 goes to Step S10 to control the display device 36 to display a message or sign indicating that the BP of the patient is abnormally low. Step S10 is followed by Step S11 corresponding to the BP measuring means 60. At Step S11, the CPU 30 operates for measuring, using the inflatable cuff 10, a systolic, a mean, and a diastolic BP value $BP_{SYS}$, $BP_{MEAN}$, $BP_{DIA}$ of the patient, and controls the display device 36 to display the thus measured BP values. After Step S11, the control of the CPU 30 goes back to Step S1 and the following steps.

On the other hand, if a positive judgment is made at Step S9, the control of the CPU 30 goes to Step S12 to judge whether the cuff pressure $P_C$ has been increased up to the predetermined low pressure value $P_1$. While negative judgments are made at Step S12, Steps S5 to S12 are carried out repeatedly, so that the cuff pressure $P_C$ is gradually increased. Meanwhile, if a positive judgment is made at Step S12, the control of the CPU 30 goes to Step S13 where the CPU 30 operates the pressure control valve 16 to quickly discharge the pressurized air from the cuff 10 into the atmosphere.

Step S13 is followed by Step S14 to judge whether a predetermined BP-measurement period $T_B$ of, e.g., from 10 to 30 minutes has passed after the last BP measuring operation. Initially, a negative judgment is made at Step S14, and the control of the CPU 30 goes back to Step S1. On the other hand, if a positive judgment is made at Step S14, the control goes to Step S11 to carry out a BP measuring operation using the cuff 10.

It emerges from the foregoing description that in the present embodiment, the NPWA calculating means 62 iteratively calculates an NPWA value $S_F$ indicative of a condition of a circulatory system of a living subject; the cuff-pressure-control starting means 66 starts a cuff-pressure control of the cuff-pressure control means 68, when the absolute value of the change value $\Delta D$ calculated by the change-value calculating means 64 is greater than a predetermined reference value $D_0$; the cuff-pressure control means 68 increases the pressing pressure (cuff pressure $P_C$) of the cuff 10 being wrapped around a body portion of the living subject, up to a predetermined low pressure value $P_1$ lower than a mean BP value $BP_{MEAN}$ of the subject; the cuff-pulse-wave detecting device 27 detects a cuff pulse wave which is produced in the cuff 10 when the cuff pressure $P_C$ is increased by the cuff-pressure control means 68; the change-rate calculating means 72 calculates the rate of change $\Theta$ of respective amplitudes $A_m$ of heartbeat-synchronous pulses of the cuff pulse wave detected by the cuff-pulse-wave detecting device 27 with respect to the cuff pressure $P_C$ increased by the cuff-pressure control means 68; and the BP-abnormality judging means 74 judges, based on the rate of change $\Theta$ calculated by the change-rate calculating means 72, whether the BP of the subject is abnormal. Thus, in the present embodiment, the cuff-pressure control means 68 increases the cuff pressure $P_C$, in order to judge the abnormality of the BP of the subject, when the NPWA value $S_F$ is judged as being abnormal, i.e., there is a great possibility that the BP of the subject may be abnormal. Therefore, the present BP monitoring apparatus 8 can employ, at Step S14, a BP measurement period $T_B$ which is much longer than that employed in a conventional apparatus. Thus, in the present apparatus 8, the cuff 10 much less frequently presses the body portion of the subject. In addition, the present apparatus 8 maintains the reliability of monitoring of the BP of the subject.

The present BP monitoring apparatus 8 includes the BP measuring means 60 which measures a BP value of a living subject by changing the cuff pressure $P_C$, and the BP-abnormality judging means 74 starts, when judging that the BP of the subject is abnormal, a BP measurement of the BP measuring means 60. Thus, when the BP-abnormality judging means 74 judges that the BP of the subject is abnormal, an accurate BP value of the subject can be immediately measured by the BP measuring means 60 using the cuff 10. A medical person who attends to the subject can immediately give appropriate treatments to the subject. Even if an abnormal NPWA value $S_F$ may be found at Step S4, the present BP monitoring apparatus 8 does not immediately start a BP measurement of the BP measuring means 60, and judges whether the BP of the subject is abnormal, by increasing the cuff pressure $P_C$ up to only the predetermined low pressure value $P_1$. Accordingly, the present apparatus 8 does not frequently start a BP measurement using the cuff 10, even though the reference value $D_0$ is predetermined at a low value so as to increase the reliability of monitoring of the apparatus 8. Thus, the present apparatus 8 relieves the subject from the load of being frequently pressed by the cuff 10.

While the present invention has been described in its preferred embodiment, the invention may be otherwise embodied.

For example, although in the illustrated embodiment the NPWA calculating means 62 calculates the NPWA value $S_F$ as the index value indicative of the condition of the circulatory system of the patient and the cuff-pressure-control starting means 66 judges that the NPWA value $S_F$ is abnormal, when the absolute value of the change value $\Delta D$ calculated for the NPWA value $S_F$ is greater than the reference value $D_0$, it is possible to omit the calculation of the change value $\Delta D$ and it is possible to judge whether the NPWA value $S_F$ is abnormal, by comparing the NPWA value $S_F$ itself with a predetermined reference range or value. In the latter case, the reference range or value is so predetermined as to indicate a great possibility that an NPWA value $S_F$ is abnormal. For example, the reference value may be equal to an NPWA value $S_F$ at the time when a living subject has a systolic BP value $BP_{SYS}$ of 90 mmHg, so that the systolic BP value $BP_{SYS}$ of 90 mmHg may be judged as being abnormal by the BP-abnormal judging means 74.

While in the illustrated embodiment the NPWA value $S_F$ is calculated by the NPWA calculating means 62 as the index value indicative of the condition of the circulatory system of the patient, it is possible to employ, as the index value, a different parameter than the NPWA value $S_F$, e.g., the pulse-wave area S shown in FIG. 3, or any other parameter indicative of an amount of flow of blood in a peripheral body portion of a living subject. Meanwhile, a pulse-wave-propagation time DT that is a time needed for a pulse wave to propagate between two portions of an arterial vessel, or a pulse-wave-propagation velocity $V_M$ calculated based on the time DT is indicative of the condition of blood circulation between those two portions of the arterial vessel, and a pulse rate (i.e., heart rate) or a pulse period is indicative of the condition of blood circulation of a central part of the circulatory system of a living subject. Accordingly, a piece of pulse-wave-propagationrelating information such as a time DT or a velocity $V_M$, or a piece of pulse-relating information such as a pulse rate or a pulse period may be employed as the index value indicative of the condition of the circulatory system of the living subject.

Figure 8:
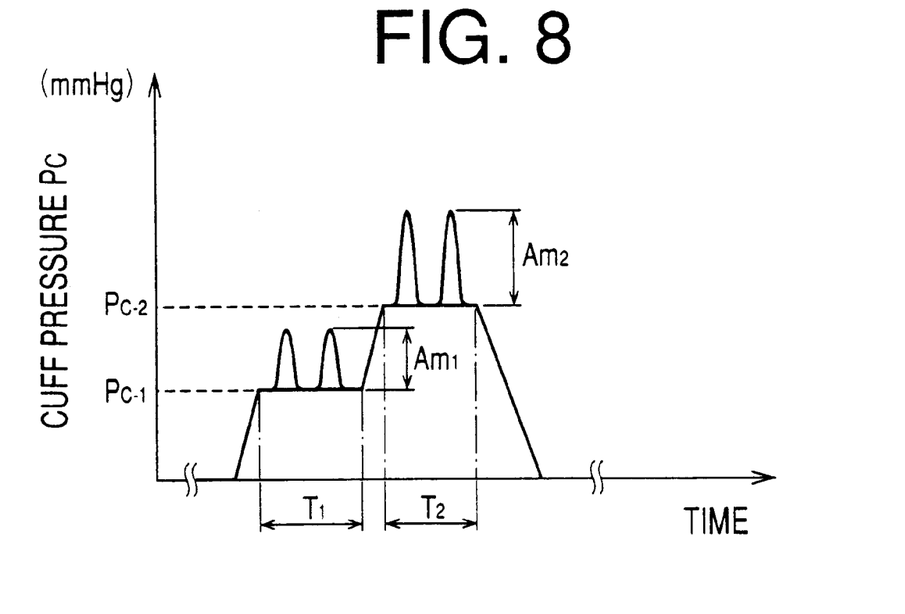
FIG. 8 is a time chart for illustrating a manner in which a pressing pressure of an inflatable cuff of another BP monitoring apparatus as a second embodiment of the present invention is changed by a pressure control means of the apparatus.

In the illustrated embodiment, the cuff-pressure-control means 68 increases the pressing pressure of the inflatable cuff 10, i.e., the cuff pressure $P_C$ up to the predetermined low pressure value $P_1$, and the change-rate calculating means 72 calculates the rate of change $\Theta$ of respective amplitudes $A_m$ of heartbeat-synchronous pulses of the cuff pulse wave detected during the increasing of the cuff pressure $P_C$. However, the cuff-pressure-control means 68 may be modified to increase the cuff pressure $P_C$ in a manner as shown in FIG. 8. More specifically described, the control means 68 may first increase the cuff pressure $P_C$ to the first predetermined pressure value $P_{C-1}$ and hold the pressure $P_C$ at the first value $P_{C-1}$ for a predetermined time period $T_1$ corresponding to not less than one heartbeat-synchronous pulse of the cuff pulse wave, then increase the pressure $P_C$ to the second predetermined pressure value $P_{C-2}$ and hold the pressure $P_C$ at the second value $P_{C-1}$ for a Adpredetermined time period $T_2$ corresponding to not less than one heartbeat-synchronous pulse, and finally decrease the pressure $P_C$ to the atmospheric pressure. In the latter case, the change-rate calculating means 72 may be modified to calculate the rate of change $\Theta$ ($=\Delta A_m/\Delta P_C$) by dividing a difference $\Delta A_m$ between a pulse amplitude $A_{m2}$ obtained in the second time period $T_2$ and a pulse amplitude $A_{m1}$ obtained in the first time period $T_1$, by a difference $\Delta P_C$ between the second and first pressure values $P_{C-2}$, $P_{C-1}$.

In the illustrated embodiment, the BP measuring means 60 measures the BP values of the patient according to the well-known oscillometric method. However, the BP measuring means 60 may be modified to measure one or more BP values of a living subject according to the well-known Korotkoff-sound method, i.e., based on the first and last detection of Korotkoff sounds during the changing of the cuff pressure $P_C$. In the latter case, a microphone for detecting the Korotkoff sounds from an upper arm of the subject is employed for use with the cuff 10, and is connected to the control device 28.

In the illustrated embodiment, the cuff-pressure-control starting means 66 judges whether or not to start a cuff-pressure control of the cuff-pressure control means 68, based on each NPWA value $S_F$ successively calculated from each of successive heartbeat-synchronous pulses of the PPW detected by the PPW sensor 40. However, the starting means 66 may be modified to judge whether or not to start a cuff-pressure control of the control means 68, based on every second or third NPWA value $S_F$ iteratively or continually calculated from every second or third pulses of the PPW, or an NPWA value $S_F$ calculated at predetermined regular intervals of, e.g., from several seconds to several tens of seconds.

It is to be understood that the present invention may be embodied with other changes, improvements, and modifications that may occur to the person skilled in the art without departing from the scope and spirit of the invention defined in the appended claims.

What is claimed is:

1. A blood-pressure monitoring apparatus comprising:
   an inflatable cuff adapted to apply a pressing pressure to a body portion of a living subject;
   a cuff-pulse-wave detecting device which detects a cuff pulse wave which is produced in the inflatable cuff when the inflatable cuff applies the pressing pressure to the body portion of the living subject, the cuff pulse wave comprising a plurality of heartbeat-synchronous pulses;
   a pressure control device which increases the pressing pressure of the inflatable cuff to a predetermined value lower than a mean blood-pressure value of the living subject;
   index-value calculating means for iteratively calculating an index value indicative of a condition of a circulatory system of the living subject;
   starting means for judging whether each of the index values calculated by the index-value calculating means is abnormal and, when said each index value is judged as being abnormal, starting the pressure control device to increase the pressing pressure of the inflatable cuff to the predetermined value;

change-rate calculating means for calculating a rate of change of respective amplitudes of the heartbeat-synchronous pulses of the pulse wave detected by the pulse-wave detecting device when the pressing pressure of the inflatable cuff is increased to the predetermined value by the pressure control device, with respect to the pressing pressure of the inflatable cuff increased by the pressure control device; and abnormality judging means for judging, based on the calculated rate of change, whether the living subject has an abnormal blood-pressure value.

2. An apparatus according to claim 1, further comprising a measuring device which measures a blood-pressure value of the living subject by changing the pressing pressure of the inflatable cuff, wherein the abnormality judging means comprises starting means for starting, when the living subject is judged as having the abnormal blood-pressure value, a blood-pressure measurement of the measuring device.

3. An apparatus according to claim 1, further comprising a periodically measuring device which periodically measures, at a predetermined period, a blood-pressure value of the living subject by changing the pressing pressure of the inflatable cuff.

4. An apparatus according to claim 1, wherein the index-value calculating means comprises:

a volumetric-pulse-wave sensor which detects a volumetric pulse wave from a peripheral body portion of the living subject, the volumetric pulse wave comprising a plurality of heartbeat-synchronous pulses; and pulse-wave-area-relating-value calculating means for iteratively calculating, as said each index value, a value relating to an area of each of the heartbeat-synchronous pulses of the volumetric pulse wave.

5. An apparatus according to claim 1, wherein the starting means comprises:

change-value calculating means for iteratively calculating a change value relating to a change of said each index value from a value based on at least one prior index value;

judging means for judging, when the calculated change value does not fall within a reference range, that said each index value is abnormal; and control means for starting the pressure control device to increase the pressing pressure of the inflatable cuff to the predetermined value.

6. An apparatus according to claim 1, wherein the change-rate calculating means comprises a memory which stores the respective amplitudes of the heartbeat-synchronous pulses of the pulse wave detected by the pulse-wave detecting device when the pressing pressure of the inflatable cuff is increased to the predetermined value by the pressure control device.

7. An apparatus according to claim 1, wherein the abnormality judging means comprises judging means for judging, when the calculated rate of change is greater than a predetermined value, that the living subject has the abnormal blood-pressure value.

8. An apparatus according to claim 1, wherein the abnormality judging means comprises judging means for judging that the living subject has the abnormal blood-pressure value, when a greatest one of the respective amplitudes of the heartbeat-synchronous pulses of the pulse wave detected by the pulse-wave detecting device when the pressing pressure of the inflatable cuff is increased to the predetermined value by the pressure control device is smaller than a predetermined value.

9. An apparatus according to claim 1, further comprising an informing device which informs, when the abnormality judging means judges that the living subject has the abnormal blood-pressure value, a person of an occurrence of abnormality to the blood pressure of the living subject.

10. An apparatus according to claim 1, wherein the starting means comprises judging means for judging that said each index value is abnormal, when a value based on said each index value satisfies a predetermined condition with respect to at least one predetermined value.

11. An apparatus according to claim 1, wherein the abnormality judging means comprises judging means for judging that the living subject has the abnormal blood-pressure value, when the calculated rate of change satisfies a predetermined condition with respect to at least one predetermined value.

12. A blood-pressure monitoring apparatus comprising:

an inflatable cuff adapted to apply a pressing pressure to a body portion of a living subject;

a cuff-pulse-wave detecting device which detects a cuff pulse wave which is produced in the inflatable cuff when the cuff applies the pressing pressure to the body portion of the living subject, the cuff pulse wave comprising a plurality of heartbeat-synchronous pulses;

a pressure control device which increases the pressing pressure of the inflatable cuff to a predetermined value lower than a mean blood-pressure value of the living subject;

index-value calculating means for iteratively calculating an index value indicative of a condition of a circulatory system of the living subject;

starting means for judging whether each of the index values calculated by the index-value calculating means is abnormal and, when said each index value is judged as being abnormal, starting the pressure control device to increase the pressing pressure of the inflatable cuff to the predetermined value; and abnormality judging means for judging whether the living subject has an abnormal blood-pressure value, based on at least one of respective amplitudes of the heartbeat-synchronous pulses of the pulse wave detected by the pulse-wave detecting device when the pressing pressure of the inflatable cuff is increased to the predetermined value by the pressure control device.

13. An apparatus according to claim 12, further comprising change-rate calculating means for calculating a rate of change of the respective amplitudes of the heartbeat-synchronous pulses of the pulse wave detected by the pulse-wave detecting device when the pressing pressure of the inflatable cuff is increased to the predetermined value by the pressure control device, with respect to the pressing pressure of the inflatable cuff increased by the pressure control device, wherein the abnormality judging means comprises judging means for judging, based on the calculated rate of change, whether the living subject has the abnormal blood-pressure value.

14. An apparatus according to claim 12, wherein the abnormality judging means comprises judging means for judging whether the living subject has the abnormal blood-pressure value, based on a greatest one of the respective amplitudes of the heartbeat-synchronous pulses of the pulse wave detected by the pulse-wave detecting device when the pressing pressure of the inflatable cuff is increased to the predetermined value by the pressure control device.

* * * * *